United States Patent [19]
Kalb et al.

[11] Patent Number: 5,509,889
[45] Date of Patent: *Apr. 23, 1996

[54] PRODUCT AND METHOD TO TREAT FEMALE INCONTINENCE

[76] Inventors: Irvin M. Kalb, 327 Alta Ave., Santa Monica, Calif. 90402; Robert H. Shaw, 243 Peck Dr., Beverly Hills, Calif. 90212; Michael J. Ram, One Horseshoe Rd., Bell Canyon, Calif. 91307

[*] Notice: The portion of the term of this patent shall not extend beyond the expiration date of Pat. No. 5,352,182.

[21] Appl. No.: 471,788

[22] Filed: Jun. 6, 1995

Related U.S. Application Data

[63] Continuation-in-part of Ser. No. 284,260, Aug. 2, 1994, which is a continuation-in-part of Ser. No. 888,597, Oct. 4, 1994, Pat. No. 5,352,182.

[51] Int. Cl.⁶ ........................................................ A61F 2/02
[52] U.S. Cl. ........................... 600/30; 604/55; 604/93; 604/247; 606/193
[58] Field of Search ............... 604/96–106, 93, 604/246, 247, 55, 329–330; 600/29–31; 606/191, 192, 193, 194

[56] References Cited

U.S. PATENT DOCUMENTS 5,352,182  10/1994  Kalb et al. ............................ 600/30

*Primary Examiner*—C. Fred Rosenbaum
*Assistant Examiner*—Chalin Smith

[57] ABSTRACT

A system for controlling drainage of the female bladder comprising a valved catheter, a stylet for placing the catheter in the female urethra, and a spike for opening the valve in the catheter to allow voiding of the contents of the bladder. The system also includes a sizing device for determining the length of the urethra so that the proper fitting catheter is used. The catheter comprises a hollow shaft with a extendable holding portion on one end for placement through the urethra and a crown on the other end for placement external of the body. The valve nay integral with the shaft or insertable after the catheter is placed in the urethra.

3 Claims, 5 Drawing Sheets

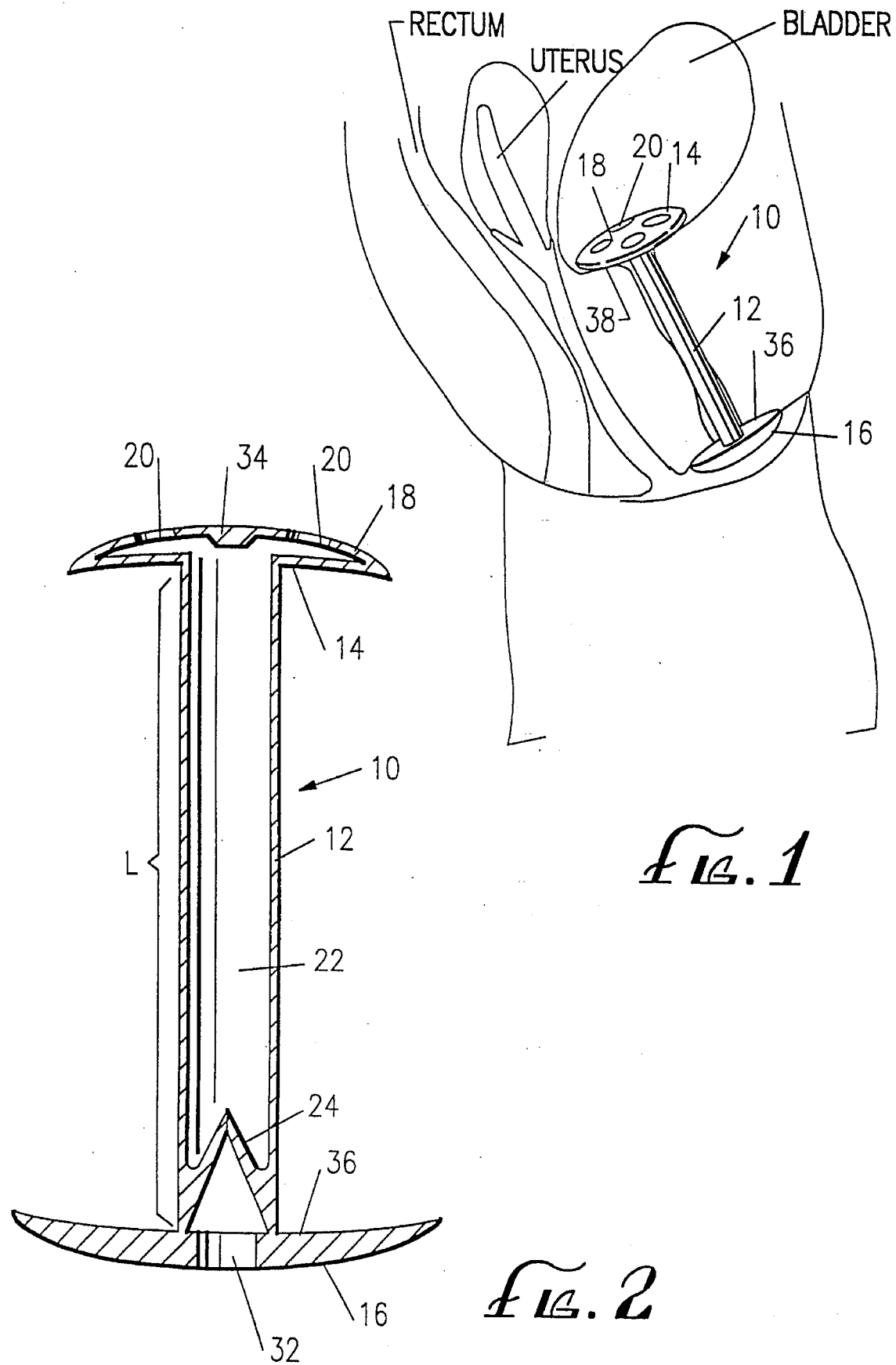

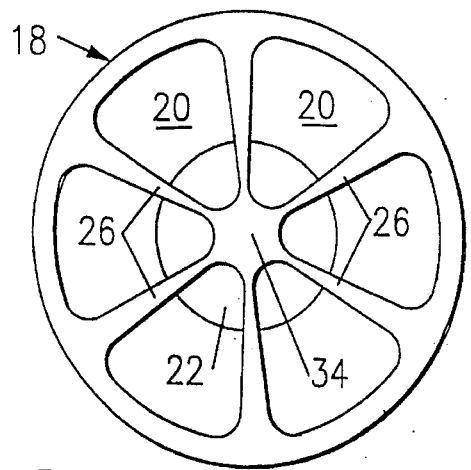
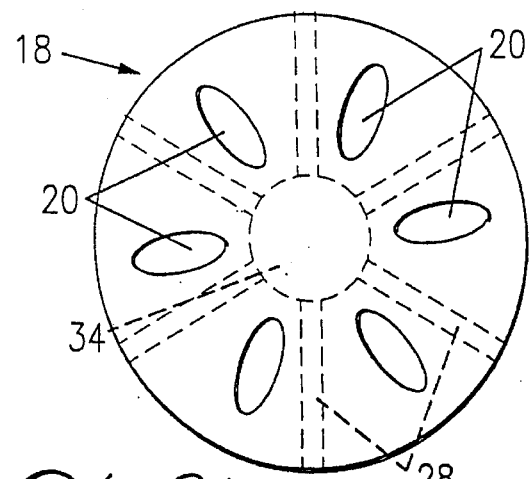
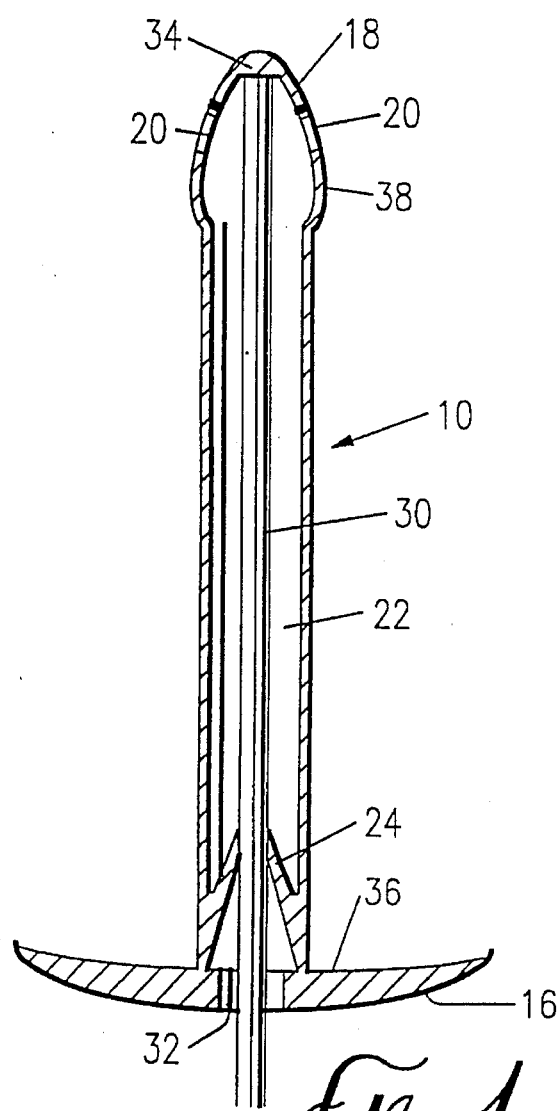
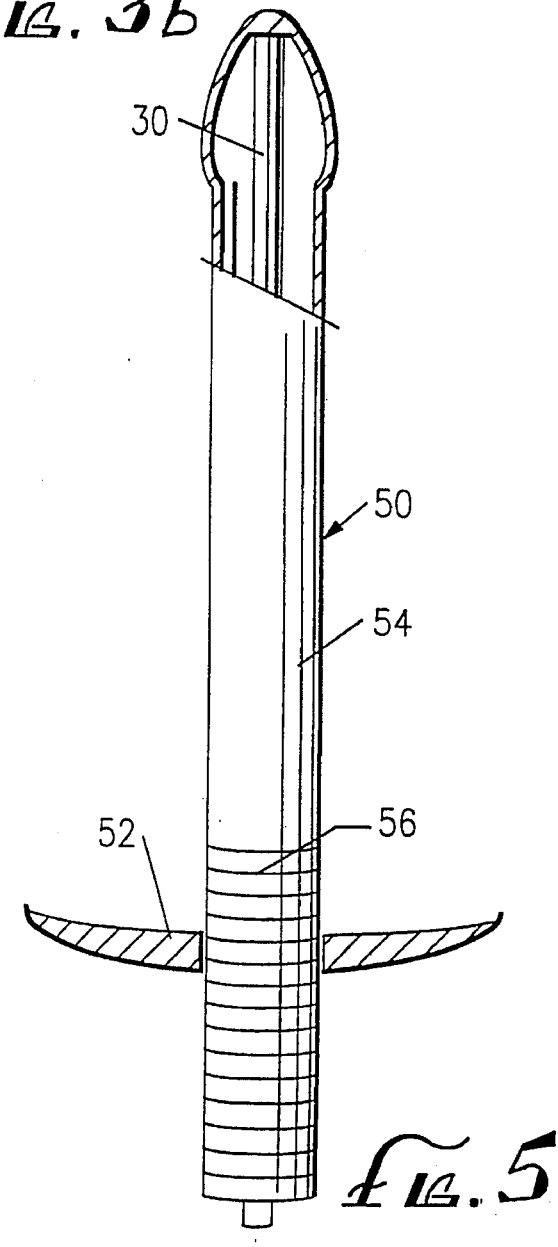

PRODUCT AND METHOD TO TREAT FEMALE INCONTINENCE

This is a continuation-in-part application of U.S. application Ser. No. 08/284,260 filed on Aug. 2, 1994, which is a continuation-in-part of application Ser. No. 888,597 filed Oct. 4, 1994, now U.S. Pat. No. 5,352,182. The present invention relates to a device and a method to control urination in an incontinent female.

BACKGROUND

A wide spread medical problem suffered by at least 11 million American adults, particularly women is incontinence. Many more suffer from the problem but, because of embarrassment or because the problem is only intermittent,, don't disclose their lack of bladder control. There are numerous causes including pregnancy, stress, as well as the normal aging process.

There presently are no adequate non-surgical techniques for treating this problem. Catheters with an attached bags are uncomfortable and are known to lead to urinary infection. Pads may be effective for small urinary leakage, such as occurs under stress, but are not suitable for large volumes of urine evacuated from a full bladder. Additionally, the use of pads requires the user to carry a large supply of replacement pads. Ureteral plugs are unacceptable replacements because the user frequently will soil her hands trying to remove the device, reinsertion of the nonsterile device may lead to a bladder infection and the frequent insertion of the plug, possibly a dozen times a day, can damage the urethra and may cause bladder spasms. Plugs may also be dangerous because they totally obstruct the ureter and may result in excessive retention of urine.

Thus there is a need for a convenient, relatively clean, and frequently repeatable procedure which can be practiced by the woman, and devices which can be used in the procedure. The devices must also be safe to use, discrete, and reliable-so that the woman can participate in a normal life style without fear of embarrassing herself by accidentally voiding the contents of her bladder or constantly running to the bathroom to change pads.

SUMMARY

The present invention is directed to a device and method that supplies these needs and eliminates the deficiencies of prior devices and systems.

The device of the invention comprises a valved drainage catheter for temporary placement in the female urethra. Additionally, the system also includes a sizing device for selecting the proper length catheter, a placement device to assure that the catheter is properly positioned and instruments to aid in opening the valve in the catheter.

The catheter comprises a hollow tube with an extendable mushroom head on the internal end, a mushroom shaped cap on the external end and a manually openable valve between the internal end and the external end to prevent urine from exiting the catheter prematurely. The sizing device is of similar shape as the drainage catheter except the catheter has a longer length, the outer surface has measurement indicia spaced along its length and the mushroom cap is replaced by a removable disc shaped similar to the mushroom cap. After insertion of the sizing device in the urethra, the disc is slid along the external portion of the catheter until it rest snugly against the perineal area. The indicia exposed below the disc indicates the correct catheter length for a proper fit.

To place the catheter, the system includes a stylet for insertion into the catheter. Drainage is accomplished by using specially designed valve openers.

DRAWINGS

These and other features, aspects and advantages of the present invention will become better understood with reference to the following description, appended claims, and accompanying drawings, where:

FIG. 1 is a side view showing the drainage catheter placed in the urethra of a female, the female body being shown in cross section.

FIG. 2 is a cutaway side view of the drainage catheter taken along line 2—2 of FIG. 1.

FIG. 3a is a top view of a first embodiment of the internal end of the drainage catheter of FIG. 2.

FIG. 3b is a top view of a second embodiment of the internal end of the drainage catheter of FIG. 2.

FIG. 4 is a cutaway side view of the drainage catheter taken along line 2—2 of FIG. 1, the catheter being extended for placement.

FIG. 5 is partial cutaway view of a sizing device.

DESCRIPTION

Figure 6:
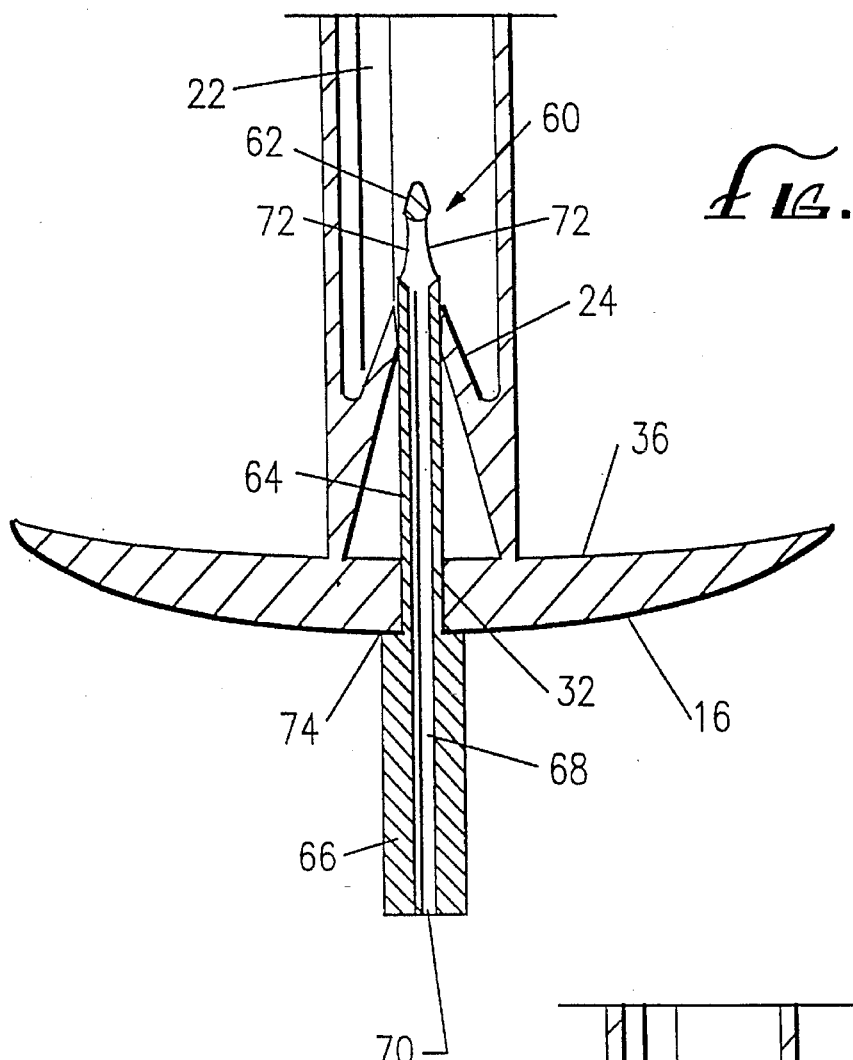
FIG. 6 is an enlarged cutaway side view of the valve section of the drainage catheter of FIG. 2 with a drainage straw inserted.

FIGS. 1 through 4 show a drainage catheter embodying features of the invention.

The drainage catheter 10 includes a tubular center section 12 with a holding portion on the internal end 14 and a cap 16 on the external end. In the embodiment shown in FIG. 2, the holding portion is a mushroom shaped crown 18 which can be extended for placement of the catheter. The crown has several drainage holes 20 located in its upper surface. Enclosed in the lumen 22 of the catheter is a one way valve 24 which can be opened by the woman using the catheter 10. In the center of the cap is an drainage outlet 32.

Alternate designs for the top surface of the crown 18 are shown in FIGS. 3a and 3b. FIG. 3a shows six large drainage holes 20 separated by spokes 26. FIG. 3b shows a similar crown 18 design having smaller holes 20 in the crown surface 28. Shown in phantom in FIG. 3b are struts which depend from the lower or inner surface of the crown 18 to assure that drainage through the holes 20 and into the lumen 22 is not blocked.

Figures 10, 11:
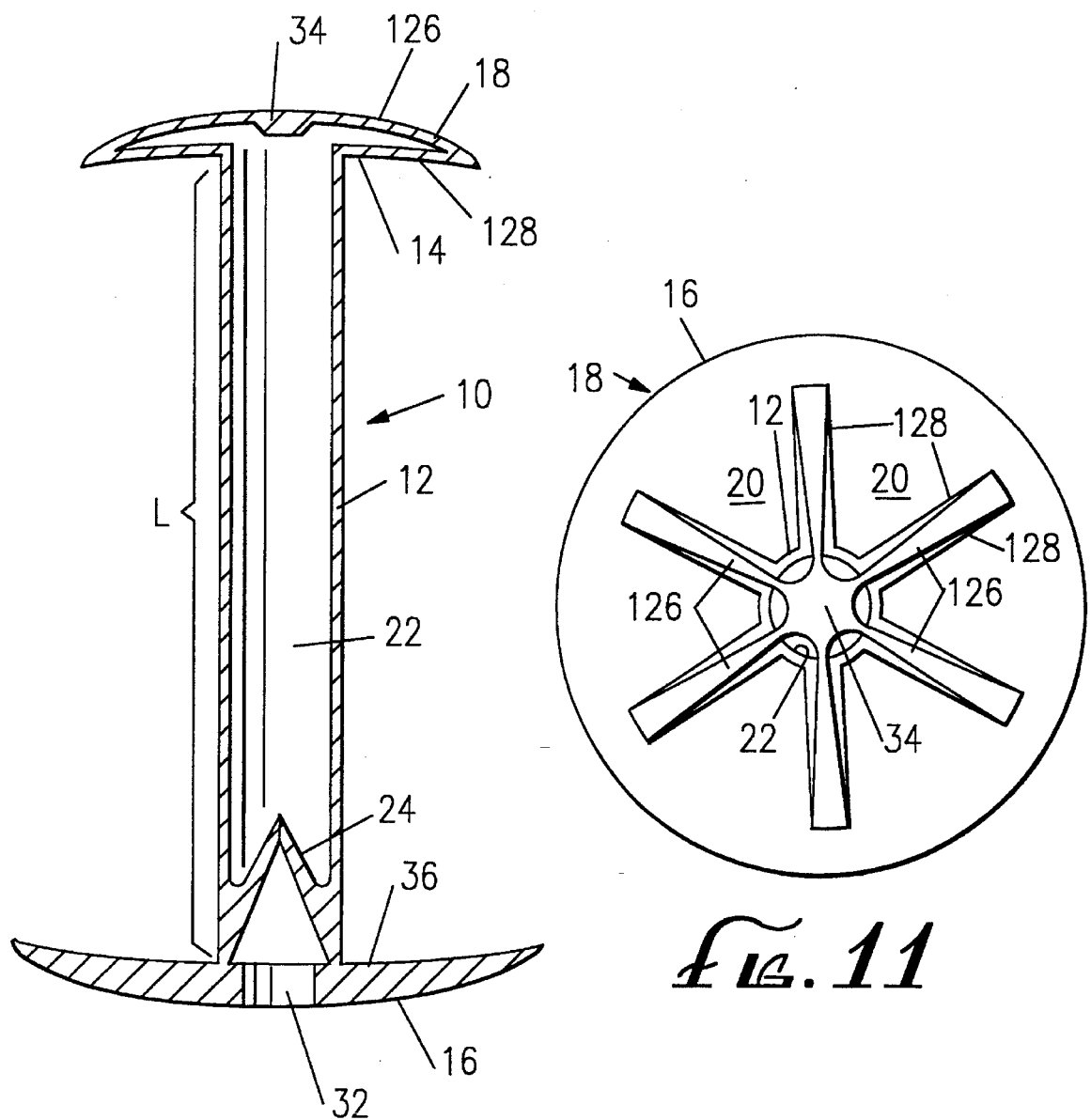
FIG. 10 is a cutaway view of a variation of the drainage catheter shown in FIG. 1.
FIG. 11 is a top view of the embodiment of FIG. 10 showing the internal end of the drainage catheter.

A further alternative design of the crown 18 is shown in FIGS. 10 and 11. FIG. 10 differs from FIG. 2 in that the hole 20 is not shown, the cross section being along the center of the spokes 126, 128. As shown in FIG. 11 the spokes 126 extend across the top of the mushroom shaped crown as well as continuing as lower spokes 128 along the bottom surface of the crown. Clinical experimentation has shown that it is not necessary that there be an uninterrupted surface resting against the neck of the bladder to result in a liquid tight seal of the catheter, the physiology of the bladder neck and urethra cooperating to create an adequate seal. FIG. 11 shows six struts 126, 128. Clinical experimentation has shown that four struts are acceptable. However, fewer or more struts can be used. FIG. 11 shows the upper struts 126 to be tapered while the lower struts 128 are shown to be wider. These differences in shape or size are for ease of illustration and not meant to limit the configuration of the struts. In clinical test samples the upper and lower struts are straight and of the same width.

Figure 7:
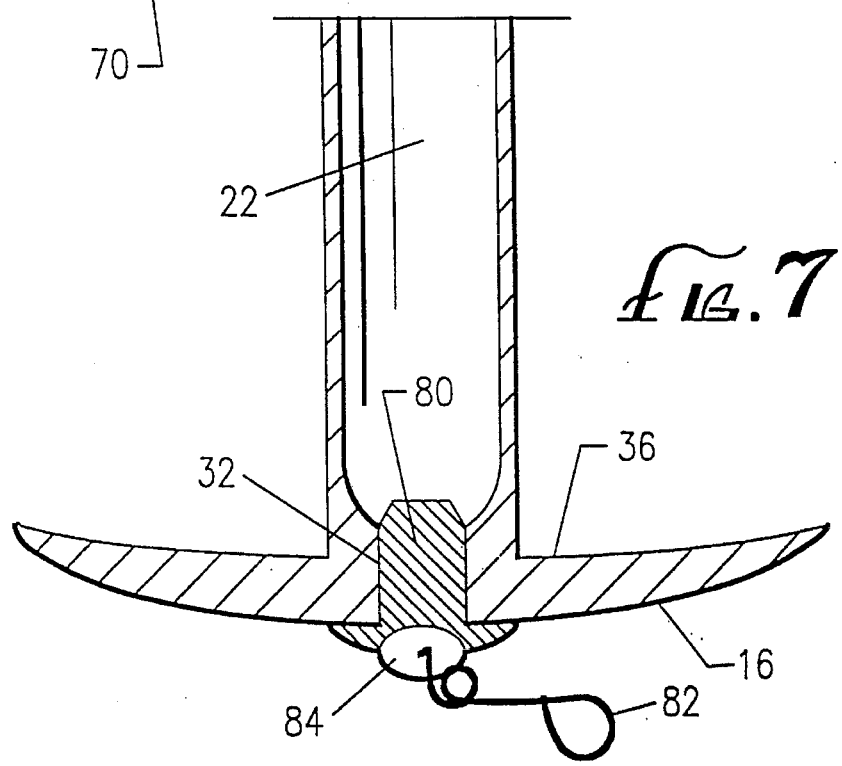
FIG. 7 is an enlarged cutaway side view of the valve section of the drainage catheter of FIG. 2 showing an alternative construction with a plug inserted.
Figure 8A:
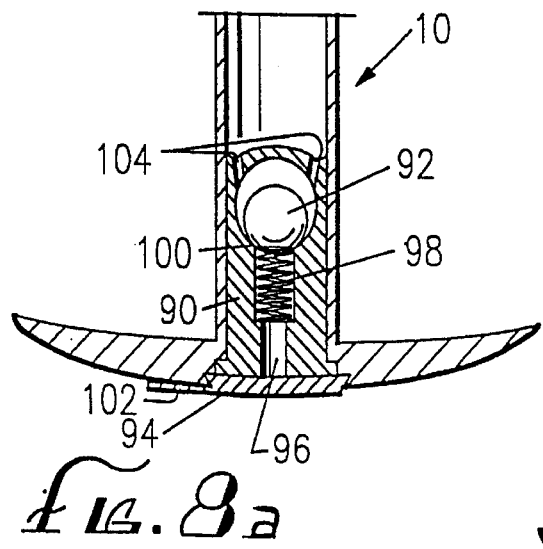
FIG. 8a is an enlarged cutaway side view of the valve section of the drainage catheter of FIG. 2 showing an alternative construction with a magnetic ball valve inserted, the valve being in its closed position.
Figure 8B:
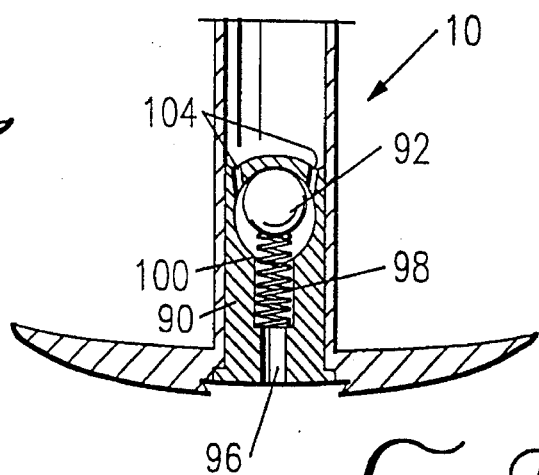
FIG. 8b is an enlarged cutaway side view of the alternative valve section of FIG. 8a in its open position.

The valve 24 shown in FIGS. 2 and 4 is of a duck bill design which prevents fluid from descending down the tube unless the valve is purposefully opened. FIGS. 7, 8a and 8b show two alternative valve structures which will be discussed below.

To insert the catheter 10 into the female urethra a stylet 30 is inserted through the drainage outlet 32 and valve 24 until it comes in contact with the reinforced center 34 of the crown 18. The stylet 30 is then advanced further extending the crown 18 until the diameter of the outer surface of the crown is about the same as the diameter of the catheter 10. The extended crown 18 is then inserted through the external opening of the ureter and advanced until it enters the bladder. If the catheter is properly sized, the inner surface 36 of the cap 16 should be resting snugly against the skin surrounding the external opening of the ureter. Insertion of the catheter 10 may be assisted by applying a small amount of a sterile lubricant to the crown 18. The styler 30 is then removed while the cap 16 is held in place. Removal of the stylet 30 allows the crown 18 to return to its normal shape with the crown inner surface 38 resting against the bladder surface as shown in FIG. 1.

In order to minimize or eliminate leakage around the catheter 10 the length L from the crown inner surface 38 to the cap inner surface 36 should be accurately determined. To do so the sizing device 50, shown in FIG. 5, is used. The sizer 50 is of substantially the same shape and has the same outer dimensions as the catheter 10 with the exception that the sizer is longer in length than the catheter 10. However, in place of the cap 16 the sizer 50 has a removable disk 52 which can slide along the outer surface of the sizer tube 54. At least a portion of the tube outer surface has indicia 56 thereon for use in selecting the proper catheter length L. Using the stylet 30 the sizer 50 is inserted into the ureter and the crown is allowed to prolapse against the bladder neck. The disc 52 is then slid along the sizer outer surface until it rests snugly against the tissue surrounding the ureter and the measurement marked on the outer surface of the tube 54 is read. The measurement indicates the catheter size to use for proper fit.

FIG. 6 shows the valve section of the catheter of FIG. 2 greatly enlarged to show the functioning of the valve during a drainage procedure. To drain the bladder a sterile spike 60 is inserted through the drainage outlet 32 in the external end of the implanted catheter 10 . The spike 60 has a center portion 64 sized to fit snugly in the drainage outlet 32 and to open the valve 24. The spike 60 has a tapered head 62 on the top end of the tubular center portion 64 and an enlarged diameter handle 66 on the lower portion. Ports 72 are located at the juncture of the head 62 with the central portion 64. A central lumen 68 starts at the ports 72 and runs the length of the spike 60 terminating in an opening 70 at the base of the handle 66. While the diameter of the central portion 64 is sized to fit snugly through the drainage port 32, the handle diameter is chosen so that it will not easily enter the drainage port 32, thus preventing the head 62 of the spike from being inserted to far into the catheter 10 and damaging the crown 18 or the bladder. Additionally, the combined length of the head 62 and the central portion 64 is chosen so that when the top end 74 of the handle 66 rests against the drainage opening 32, the head 62 pierces the drainage outlet 32 and the valve 24, exposing the ports 70 to a standing column of urine in the catheter 10 above the valve 24. This cooperation of parts allows the user to drainage the bladder without soiling her hands from leaking urine. Once drainage is complete the spike is withdrawn and the valve closes and seals. The spike can then be disposed of or resterilized.

FIG. 7 shows and alternate valve mechanism comprising a plug 80 sized to fit in the drainage opening 32. The plug can be used in place of the valve 24 (as shown in FIG. 7) or in combination with the valve 24 as additional protection against leakage (not shown). The plug is shown with a draw string 82 and a pull tab 84.

FIGS. 8a and 8b shows the catheter 10 with a ball valve mechanism 90 inserted in the external end of a drainage catheter 10. The catheter 10 is shown to have a uniform inner diameter along it entire length. After insertion of the catheter 10 using the styler 30 and removal of the stylet the ball valve 90 is placed and secured in the catheter 10. The ball valve 90 comprises a ball 92 which is attracted by a magnetic disc 94 placed over the drainage outlet 96. Also enclosed in the valve 90 is a spring 98 which lifts the ball 92 off the seat 100 when the magnetic disc 94 is removed. To raise the ball 92 off the seat 100 the tab 102 is grasped and pulled downward. The removal of the magnetic force allows the spring to lift the ball 92 unsealing the drainage outlet 96 so that the urine can flow through the valve openings 104 and out the catheter 10.

Figure 9A:
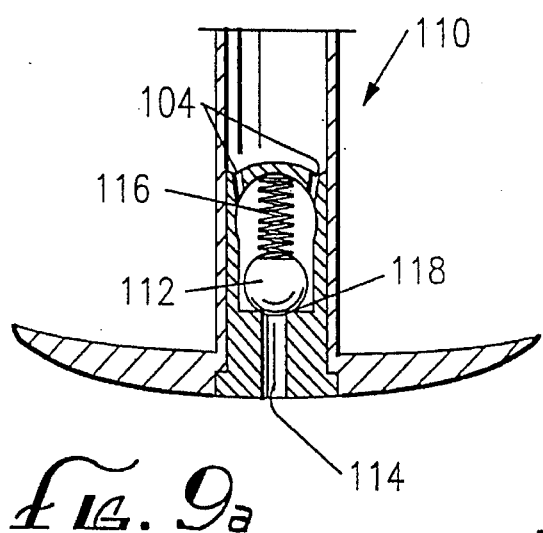
FIG. 9a is an enlarged cutaway view of the valve section of the drainage catheter of FIG. 2 showing a second alternative ball valve structure in its closed structure.
Figure 9B:
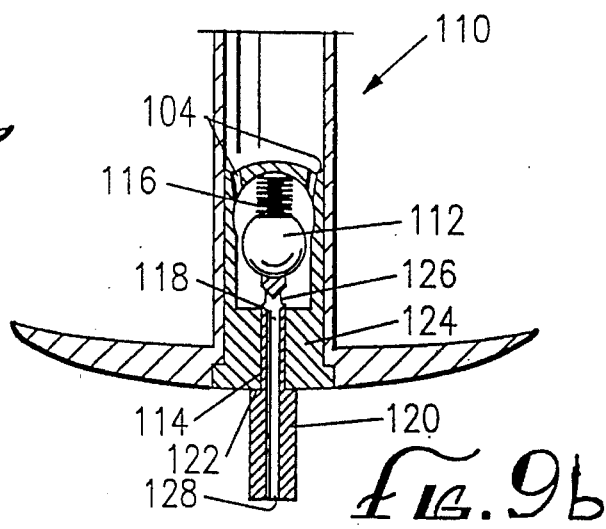
FIG. 9b is an enlarged cutaway side view of the second alternative valve section of FIG. 9b in its open position.

FIGS. 9a and 9b shows the catheter 10 with a ball valve mechanism 110 inserted in the external end of a drainage catheter 10. Like the embodiment shown in FIGS. 8a and 8b, the catheter is also shown to have a uniform inner diameter along its entire length. The valve mechanism 110 is inserted into the catheter 10 after its placement in the urethra. The ball valve 110 comprises a ball 112 which is held against the drainage opening 114 by the spring 116. To raise the ball 112 off the seat 118 a spike 120 is inserted through the drainage opening 114 until the shoulder 122 contacts the bottom 124 of the valve, compressing the spring 116 allowing urine to flow through the valve 110, ports 126 and drainage channel 128 through the center of the spike 120.

The catheter 19 can be fabricated from a broad range of materials presently used for forming urinary catheter including, but not limited to, natural and synthetic rubbers, silicone rubbers, thermoplastic elastomers, latex, polyvinyl chloride, polyethylene, and PTFE with or without coatings such as silicone materials, Teflon, hydrophilic compounds and other materials which improve the compatibility with mucosal tissue. Additionally, antibacterials, anti-inflammatory drugs, antibiotics or other drugs can be coated on the catheter surface or absorbed into the coatings on the catheter surface. In the embodiment of FIGS. 8a and 8b, the ball 92 is a magnetic material, preferentially a plastic material having magnetic materials or magnetizable materials dispersed therein or ceramometallic materials. The spike 66 or 120 may be formed from a broad range of materials. Stiffness during use is the primary design criteria. Secondly, since the spike is intended to be disposable, the material should be inexpensive. While materials like polyethylene or polypropylene are suitable, a particularly preferred material is a material slowly dissolvable in water or biodegradable so that the spike can be disposed of into the toilet without clogging the plumbing system.

The dimensions of the catheter are dependent on the dimensions of the anatomy of the patient into which the catheter is being placed. The outer diameter of the tubular section 12 of the catheter is about 8 mm and the effective length between the cap 16 and the crown 18 is between about 2.5 and 4.5 cm. However, as indicated, the dimensions can be selected to create a non-leak seal with the patients urinary tract. The diameter of the cap and the crown is from about 12 to 17 mm.

The present invention has been described in considerable detail with reference to certain preferred versions and uses thereof, other versions and uses are possible. Other valves designs, dimensions, materials or crown designs may be used without changing the inventive concept. Therefore, the scope of the appended claims should not be limited to the description of the preferred versions contained herein.

What is claimed is:

1. A urinary drainage catheter for placement in the female urethra, the urethra having an exterior opening at the point of exit from the body and an interior opening at the point of entry into the urinary bladder, the catheter comprising a hollow shaft, a holding portion on a first end of the shaft and a cap on a second end of the shaft, wherein:

the shaft has a length sized to approximate the length of the urethra and an outer diameter approximating the diameter of the urethra such that the shaft does not extend beyond the exterior of the urethra, the holding portion having
a) upper and lower struts separated by openings therebetween so that fluid in the bladder can enter the shaft, and
b) a width greater than the outer diameter of the shaft, the width of the holding portion being reducible so that the holding portion can be readily passed through the urethra, lower struts of said holding portion resting against the interior end of the urethra, and the cap having a width greater than the outer diameter of the shaft, an upper surface of said crown resting against the exterior opening of the urethra, no portion of the urinary catheter extending exterior of the urethra cap.

2. The urinary drainage catheter of claim 1 further including a valve within the hollow shaft to control flow of fluid through the catheter.

3. A urinary drainage control system comprising a valved urinary drainage catheter for placement in the female urethra, the urethra having an exterior opening at the point of exit from the body and an interior opening at the point of entry into the urinary bladder, a stylet for use in placing the catheter, and a hollow spike for opening the valve to allow drainage of fluid from the bladder, the catheter comprising a hollow shaft with a lumen longitudinally through its center, a holding portion on a first end of the shaft, a cap on a second end of the shaft, no portion of the urinary drainage catheter extending exterior of the urethra beyond the cap, and a valve located within the lumen of the shaft, wherein:

the shaft has a length approximating the length of the urethra and an outer diameter approximating the diameter of the urethra such that the second end of the shaft is located at the exterior opening of the urethra, the holding portion has a width greater than the outer diameter of the shaft, there being openings through the holding portion so that fluid in the bladder can enter the shaft lumen, the width of the holding portion being reducible so that the holding portion can be readily passed through the urethra, the cap has a hole therethrough in line with the lumen of the shaft and a width greater than the outer diameter of the shaft, the stylet is a stiff rod with a diameter less than the inner diameter of the shaft and a length greater than the length of the catheter such that insertion of the stylet through the lumen of the catheter and pushing the styler against the holding portion causes the holding portion to elongate and the width to reduce to a diameter suitable for passing through the urethra, the spike having an insertion portion, an exterior portion, a flange on an outer surface thereof separating the insertion portion from the exterior portion, a diameter approximating the inner diameter of the shaft and a length sufficient to enter the valve, the exterior portion of the spike being sized for grasping in the fingers of a user such that when the insertion portion is passed through the hole in the cap and the flange is in contact with the cap the valve opens allowing fluid to drain from the bladder through the shaft, valve and the lumen of the spike without soiling the fingers of the user.

\* \* \* \* \*